(12) United States Patent
Taniguchi et al.

(10) Patent No.: US 9,872,625 B2
(45) Date of Patent: Jan. 23, 2018

(54) AIRBAG FOR BLOOD PRESSURE MEASURING DEVICE AND METHOD OF MANUFACTURING THE SAME

(71) Applicants: OMRON HEALTHCARE Co., Ltd., Kyoto (JP); SATO IKEN CO., LTD., Tokyo (JP)

(72) Inventors: Minoru Taniguchi, Kyoto (JP); Satoshi Doi, Kyoto (JP); Yoichi Egawa, Tokyo (JP); Takashi Tone, Kyoto (JP); Tameo Ashida, Kyoto (JP); Kenichi Sato, Tokyo (JP)

(73) Assignees: OMRON HEALTHCARE Co., Ltd., Kyoto (JP); SATO IKEN CO., LTD., Tokyo (JP)

( * ) Notice: Subject to any disclaimer, the term of this patent is extended or adjusted under 35 U.S.C. 154(b) by 497 days.

(21) Appl. No.: 14/557,090

(22) Filed: Dec. 1, 2014

(65) Prior Publication Data

US 2015/0088011 A1 Mar. 26, 2015

Related U.S. Application Data

(63) Continuation of application No. PCT/JP2013/064337, filed on May 23, 2013.

(30) Foreign Application Priority Data

May 30, 2012 (JP) ................................. 2012-123191

(51) Int. Cl.
*A61B 5/022* (2006.01)
*B32B 37/18* (2006.01)
(Continued)

(52) U.S. Cl.
CPC .......... *A61B 5/02233* (2013.01); *B32B 37/18* (2013.01); *B32B 38/0012* (2013.01);
(Continued)

(58) Field of Classification Search
CPC ............ A61B 5/02233; B32B 38/0012; B32B 37/18; B32B 2535/00; B29C 53/385; B29C 53/40; Y10T 156/1051
See application file for complete search history.

(56) References Cited

U.S. PATENT DOCUMENTS 7,794,405 B2 * 9/2010 Karo .................. A61B 5/02233
                                                            600/485
9,028,419 B2 * 5/2015 Quinn ................ A61B 5/02233
                                                            600/499
(Continued)

FOREIGN PATENT DOCUMENTS

JP         S61-100228 A     5/1986
JP         2005-230175 A    9/2005
(Continued)

OTHER PUBLICATIONS

International Preliminary Report on Patentability dated Dec. 11, 2014 in related PCT Application No. PCT/JP2013/064337 (5 pages).
(Continued)

*Primary Examiner* — Meredith Weare
(74) *Attorney, Agent, or Firm* — Osha Liang LLP

(57) ABSTRACT

An airbag for a blood pressure measuring device for fixing a cuff, including: a main sheet member which spreads in two layers forming a bag body, wherein a constricted portion is formed on the bag body, the constricted portion narrowing the air chamber with respect to the width direction, a pair of sub sheet members are disposed so as to correspond to the respective layers of the main sheet member, the sub sheet member occupying a region including at least a portion corresponding to the constricted portion, and the pair are respectively welded to the layers of the main sheet member at the constricted portion, the pair being welded to the corresponding layers of the main sheet member at a center (Continued)

near portion away from the constricted portion toward a center side with respect to the width direction.

8 Claims, 11 Drawing Sheets

(51) Int. Cl.
 *B32B 38/00* (2006.01)
 *B29C 53/38* (2006.01)
 *B29C 53/40* (2006.01)
(52) U.S. Cl.
 CPC ............ *B29C 53/385* (2013.01); *B29C 53/40* (2013.01); *B32B 2535/00* (2013.01); *Y10T 156/1051* (2015.01)

(56) References Cited

U.S. PATENT DOCUMENTS

| | | | | |
|---|---|---|---|---|
| 2004/0181156 A1* | 9/2004 | Kingsford | .......... | A61B 5/02233 600/490 |
| 2004/0186385 A1* | 9/2004 | Mochizuki | ......... | A61B 5/02141 600/499 |
| 2006/0135873 A1* | 6/2006 | Karo | ................... | A61B 5/02233 600/499 |
| 2010/0268099 A1* | 10/2010 | Uesaka | .............. | A61B 5/02233 600/493 |
| 2011/0190644 A1* | 8/2011 | Kohyama | .............. | A61B 5/022 600/499 |

FOREIGN PATENT DOCUMENTS

| | | |
|---|---|---|
| JP | 2006-174860 A | 7/2006 |
| JP | 2010-088505 A | 4/2010 |

OTHER PUBLICATIONS

International Search Report issued in PCT/JP2013/064337, dated Jun. 18, 2013 (4 pages).

* cited by examiner

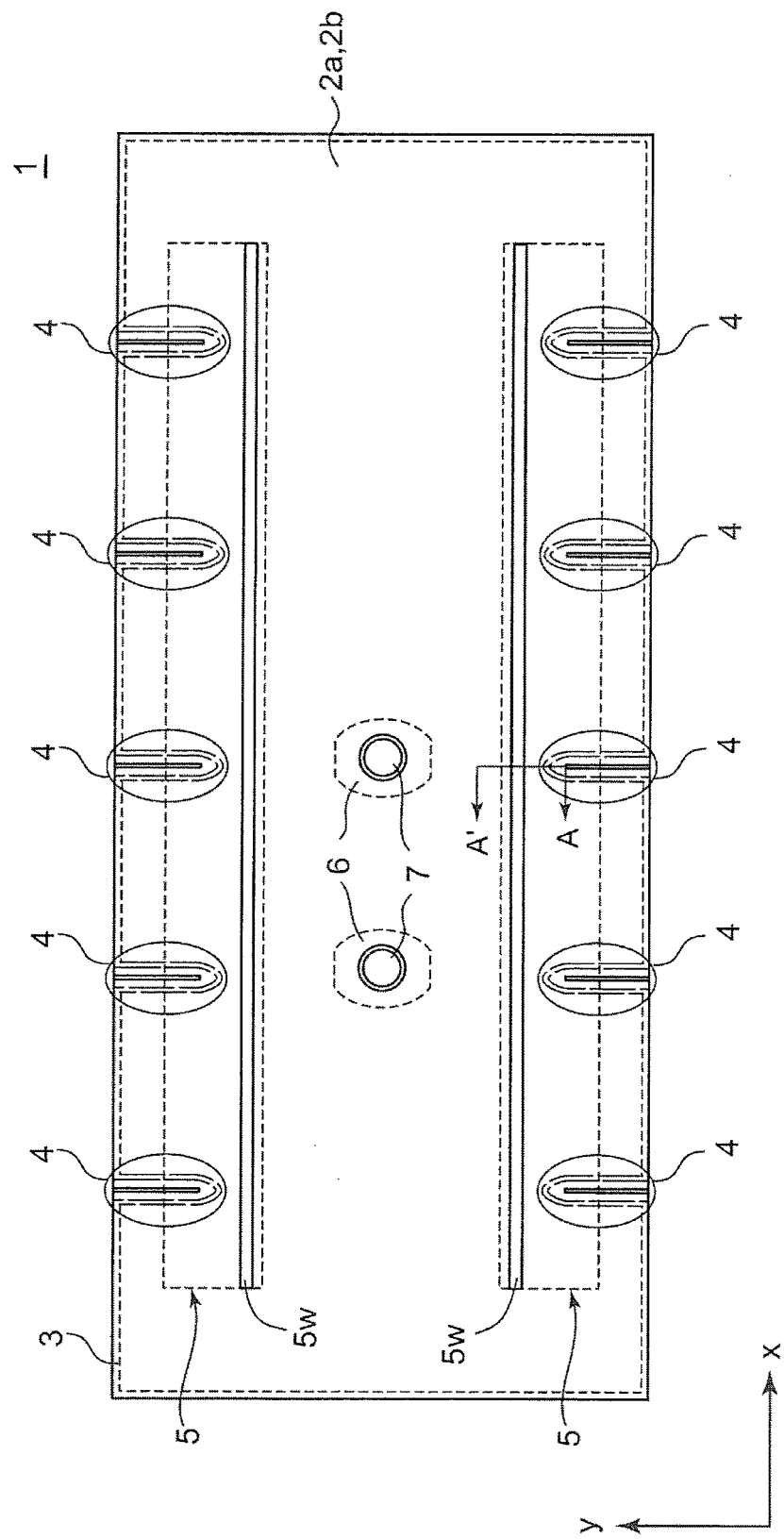

AIRBAG FOR BLOOD PRESSURE MEASURING DEVICE AND METHOD OF MANUFACTURING THE SAME

CROSS-REFERENCE TO RELATED APPLICATIONS

This is a continuation application of International Application No. PCT/JP2013/064337, with an international filing date of May 23, 2013, which claims priority of Japanese Patent Application No. 2012-123191 filed on May 30, 2012, the content of which is incorporated herein by reference.

BACKGROUND

1. Technical Field

The present invention relates to an airbag for a blood pressure measuring device, and more particularly to an airbag for a blood pressure measuring device used for fixing a cuff (pressure band) to a part to be measured.

The present invention also relates to a method of manufacturing the above-mentioned airbag for a blood pressure measuring device.

2. Related Art

Conventionally, as an airbag used for fixing a cuff (pressure band) to a part to be measured in a blood pressure measuring device, as disclosed in Patent Document 1 (JP 2005-230175 A), for example, there has been known a curler pressing airbag in which a living body pressing airbag is disposed outside a curler, and the living body pressing airbag is inflated such that an outer peripheral surface of the curler is pressed inward thus decreasing a diameter of the curler, whereby the living body pressing airbag is pressed to a part of a human body by way of the curler.

Hereinafter, this type of airbag is briefly described with reference to FIG. 6 and FIG. 7.

FIG. 6 is a schematic view showing an in-use state of a blood pressure measuring device 101 of an upper arm automatic wrapping type. In the blood pressure measuring device 101, an airbag 108 is inflated by supplying air into the airbag 108. The airbag 108 is maintained in a pressure-applied state so that a diameter of a curler 110 is decreased, whereby a cuff 113 is fixed to an upper arm portion 100 by the curler 110.

FIG. 7 is a view showing a state where the airbag 108 is inflated, and the upper arm portion 100 inserted into the blood pressure measuring device 101 is fixed by the airbag 108 and the curler 110. As shown in FIG. 7, constricted portions 104 which prevent the inflation of the airbag 108 are disposed along the circumferential direction of the airbag 108. The airbag 108 is inflated in such a manner that six projecting portions which project inward are formed by pressurized air, and peak portions of six projecting portions uniformly press the curler 110. As a result, a diameter of the pressed curler 110 is decreased so that the cuff 113 is fixed to the upper arm portion 100.

As shown in the figure, the constricted portions 104 are formed in the airbag 108 at equal intervals in the circumferential direction such that a plurality of projecting portions are formed due to the inflow of pressurized air into the airbag 108. The constricted portions 104 are formed by welding portions of opposed inner walls of the airbag 108 to each other.

As a technique related to welding, Patent Document 2 (JP 61-100228 A) discloses a cuff for measuring a blood pressure provided with a bag portion formed by welding peripheral edge portions of a pair of flexible resin sheets to each other. In Patent Document 2 (JP 61-100228 A), the bag portion is formed by welding a pair of flexible resin sheets to each other using high-frequency welding in a state where the other resin sheets are interposed between the flexible resin sheets. With such a configuration, the decrease in thickness of the flexible resin sheet caused by the welding step is compensated for by thicknesses of other interposed resin sheets so that the decrease in strength of a welded portion can be suppressed.

SUMMARY

FIGS. 8A and 8B are a partial cross-sectional view of an area in the vicinity of the constricted portion 104 of the airbag 108 taken along line B-B' in FIG. 6 and FIG. 7. To simplify the drawing, elements other than the airbag 108 are omitted in the drawings. The airbag 108 is formed by bonding peripheries (not shown) of two sheet members 108a, 108b, and the constricted portions 104 are formed by welding opposed inner walls of two sheet members 108a, 108b.

FIG. 8A is a partial cross-sectional view of the airbag 108 in a contracted state where air is discharged from the airbag 108. FIG. 8B is a partial cross-sectional view of the airbag 108 in an inflated state where pressurized air is supplied to the airbag 108 so that the airbag 108 is inflated.

Referring to FIG. 8B, in a state where pressurized air is supplied to the airbag 108, the airbag 108 is inflated by being largely bent in a region R just in the vicinity of the constricted portion 104. Accordingly, when the airbag 108 is inflated, stress concentration occurs in the regions R of the sheet members 108a, 108b. Accordingly, a large stress is applied to an area in the vicinity of the region R.

Further, referring to FIG. 8A and FIG. 8B, the airbag 108 is largely deformed (bent) in the regions R of the sheet members 108a, 108b when the airbag 108 is inflated or contracted. Accordingly, the degree of fatigue accumulated in the region R over the years is large compared to fatigue accumulated in other portions of the sheet members 108a, 108b over the years.

Accordingly, to enhance strength and durability of the airbag 108, it is important to study the enhancement of strength and durability of the airbag 108 in the vicinity of the regions R of the sheet members 108a, 108b.

As described above, Patent Document 2 (JP 61-100228 A) discloses the technique for enhancing pressure resistance of the bag portion formed by welding the pair of flexible resin sheets. However, although the technique disclosed in Patent Document 2 (JP 61-100228 A) can suppress the decrease of wall thickness of the welded portion (for example, the constricted portion 104 shown in FIGS. 8A and 8B or the like) caused by welding, the technique is not intended to enhance strength and durability of a region in the vicinity of the welded portion (for example, a region R just in the vicinity of the constricted portion 104). Accordingly, the technique disclosed in Patent Document 2 (JP 61-100228 A) cannot achieve the object of enhancing the strength of the above-mentioned region in the vicinity of the welded portion.

Accordingly, embodiments of the present invention aim to provide an airbag for a blood pressure measuring device having enhanced strength.

The embodiments of the present invention also aim to provide a method of manufacturing an airbag for a blood pressure measuring device having enhanced strength.

To solve the above problems, an airbag according to a first aspect of the present invention is an airbag for a blood pressure measuring device for fixing a blood pressure measuring cuff to an upper arm portion of a person to be measured, the airbag including:

a main sheet member which spreads in two layers in a longitudinal direction and in a width direction perpendicular to the longitudinal direction so as to form a bag body which defines an air chamber therein, wherein at least one constricted portion is formed locally on the bag body with respect to the longitudinal direction of the bag body, the constricted portion being formed by welding the two layers of the main sheet member so as to narrow a size of the air chamber with respect to the width direction, a pair of sub sheet members are disposed so as to correspond to an inside or an outside of the respective layers of the main sheet member, the sub sheet member occupying a wider region than the constricted portion including at least a portion corresponding to the constricted portion, and the pair of sub sheet members are respectively welded to the corresponding layers of the main sheet member at a portion corresponding to the constricted portion, the pair of sub sheet members being welded to the corresponding layers of the main sheet member at a center near portion away from the constricted portion toward a center side with respect to the width direction.

To solve the above problems, a method of manufacturing an airbag for a blood pressure measuring device according to a second aspect of the present invention is a method of manufacturing the airbag for a blood pressure measuring device according to the above embodiment, the method including:

a first welding of welding the two layers of the main sheet member and the corresponding sub sheet members at portions of the two layers of the main sheet member corresponding to center near portions; and a second welding of, after the first welding, forming the constricted portions by welding the two respective layers of the main sheet member and the corresponding sub sheet members at portions of the two respective layers of the main sheet member corresponding to the constricted portions and, simultaneously, forming the bag body by welding the two respective layers of the main sheet member at the peripheral edge portions of the sheet.

A method of manufacturing an airbag for a blood pressure measuring device according to a third aspect of the present invention is a method of manufacturing the airbag for a blood pressure measuring device according to the above embodiment, the method including:

a first welding of welding the respective layers of the main sheet member and the corresponding sub sheets to each other at a portion corresponding to a center near portion of one continuous sheet corresponding to the two layers of the main sheet member;

a folding of, after the first welding, folding the one continuous sheet so as to form the two layers of the main sheet member; and a second welding of, after the folding, forming the constricted portions by welding the two respective layers of the main sheet member and the corresponding sub sheet members at portions of the two layers of the main sheet member corresponding to the constricted portions and, simultaneously, forming the bag body by welding the corresponding peripheral edge portions of the folded one sheet.

BRIEF DESCRIPTION OF DRAWINGS

The embodiments of the present invention will become more fully understood from the detailed description given hereinbelow and the accompanying drawings which are given by way of illustration only, and thus are not limitative of the present invention, and wherein:

FIG. 1 is a plan view of an airbag for a blood pressure measuring device according to one embodiment of the present invention;

DETAILED DESCRIPTION

Figure 2A:
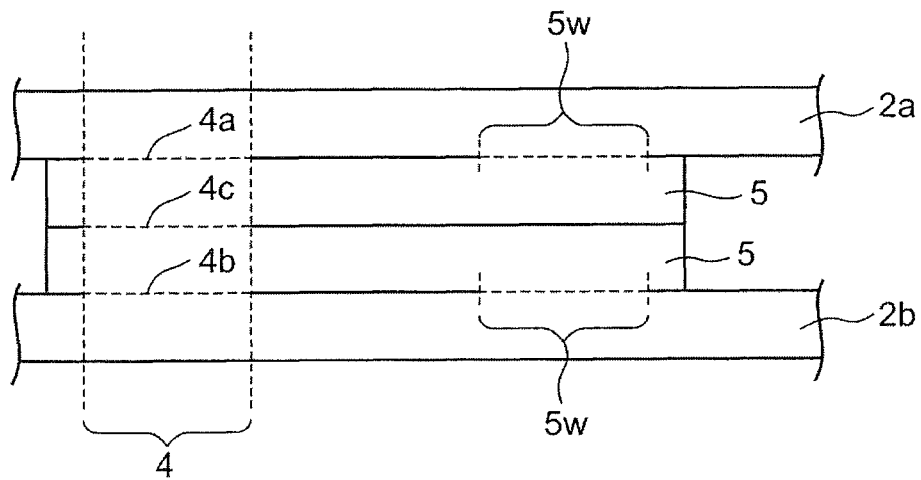
FIG. 2A is a cross-sectional view taken along line A-A' in FIG. 1 (when the airbag is not inflated)

Hereinafter, embodiments of the present invention are described in detail with reference to the drawings.

FIG. 1 is a plan view of an airbag 1 for a blood pressure measuring device according to an embodiment of the present invention. The airbag 1 for a blood pressure measuring device (hereinafter simply referred to as "airbag 1") is an airbag for a blood pressure measuring device suitable for being used as an airbag for fixing a blood pressure measuring cuff to an upper arm portion of a person to be measured. A position where the cuff is fixed is not limited to the above-mentioned upper arm portion. It is sufficient that the position where the cuff is fixed is a body part of a person to be measured. For example, the position where the cuff is fixed may be a body part such as a wrist or a lower limb.

In the airbag 1, a bag body which functions as an air chamber is formed using sheets in two layers (for example, two main sheet members 2a, 2b) which are welded to each other at peripheral edge portions 3. The main sheet member 2a has opening portions 6, and can be connected to an air supply and discharge system (not shown) through nipples 7 welded to the opening portions 6.

Constricted portions 4 which narrow a size of the air chamber in the width direction (vertical direction (y-direction) in the drawing) are formed on the airbag 1. In this embodiment, five pairs of upper and lower constricted portions 4, 4 are disposed at equal intervals in the longitudinal direction (lateral direction (x-direction) in the drawing) of the airbag 1. The constricted portion 4 is formed by welding a portion of the main sheet member 2a and a portion of the main sheet member 2b which face each other.

It is sufficient that at least one constricted portion 4 is formed on the airbag 1 in the longitudinal direction (lateral direction (x-direction) in the drawing) of the airbag 1. The number of constricted portions 4 is not limited to one, and a plurality of constricted portions 4 may be formed on the airbag 1. For example, a plurality of constricted portions 4 may be formed at equal intervals in the longitudinal direction (lateral direction (x-direction) in the drawing) of the main sheet members 2a, 2b.

A pair of sub sheet members 5 are disposed by welding on two sheet members, i.e., the main sheet member 2a and the main sheet member 2b which constitute the bag body of the airbag 1. In FIG. 1, the pair of (two) sub sheet members 5 are disposed by welding at positions of the main sheet member 2a and positions of the main sheet member 2b which correspond to each other on an inner side of the bag body. (In FIG. 1, "pair of sub sheet members" is disposed at positions which overlap with each other as viewed in a plan view.)

It is sufficient that the sub sheet member 5 is formed of a member which occupies a wider region than the constricted portions 4. The sub sheet members 5 are disposed such that at least a portion of a region of the sub sheet member 5 corresponding to the constricted portion 4 of the corresponding main sheet member 2a or 2b overlaps with the main sheet member 2a or 2b as viewed in a plan view. Further, the sub sheet members 5 are welded to the corresponding main sheet member 2a or 2b at the constricted portions 4 and a portion (center near portion) 5w away from the constricted portions toward a center side with respect to the width direction of the main sheet member 2a or 2b.

By setting a spaced-apart distance between a welded portion 4a or 4b between the main sheet member 2a or 2b and the sub sheet member 5 at the constricted portion 4, and a welded portion between the main sheet member 2a or 2b and the sub sheet member 5 at the center near portion 5w to a value equal to or larger than a sum of a wall thickness of one main sheet member 2a or 2b and a wall thickness of one sub sheet member 5, a larger strength and durability enhancing effect can be expected. Accordingly, such a distance is preferable.

It is sufficient that the wall thickness of the main sheet members 2a, 2b have substantially the equal wall thickness as a sheet member of a conventional airbag. In this case, by setting a wall thickness of the sub sheet member 5 to approximately 0.3 (mm), for example, it is expected that strength and durability of the airbag for a blood pressure measuring device can be remarkably enhanced. By setting the spaced-apart distance between the constricted portion 4 and the center near portion 5w to approximately 4.0 (mm), for example, it is expected that strength and durability of the airbag for a blood pressure measuring device can be remarkably enhanced.

The pairs of sub sheet members 5 are respectively disposed on inner sides of the bag body formed of the sheets in two layers, i.e., the main sheet members 2a, 2b. Accordingly, in the airbag 1 of this embodiment, an outer shape of the airbag 1 can be made smooth at the same level as the conventional airbag.

In this embodiment, the sub sheet member 5 is disposed so as to extend over the plurality of constricted portions 4. The sub sheet member 5 is welded to the main sheet member at the plurality of constricted portions 4 and the center near portion 5w.

By welding the sub sheet members 5 to the main sheet members 2a, 2b in this manner, the sub sheet members 5 can be disposed such that one sub sheet member 5 includes the portions corresponding to the plurality of constricted portions 4 and hence, in the manufacturing processes, the number of man-hours for positioning the sub sheet members 5 with respect to the main sheet member 2a or 2b can be reduced. Further, the number of sub sheet members 5 necessary for manufacturing the airbag 1 can be reduced. Still further, it is possible to press the curler uniformly along the circumferential direction at the time of measuring a blood pressure.

A size of the sub sheet member 5 in the direction which agrees with the width direction of the main sheet members 2a, 2b when the sub sheet members 5 are disposed on the main sheet members 2a, 2b can be set smaller than a size of the main sheet member 2a, 2b in the width direction. Accordingly, the airbag 1 of this embodiment can reduce a manufacturing cost and can also reduce a total weight of the airbag 1 compared to a case where reinforcing members having substantially the same size as the main sheet members 2a, 2b are used.

Figure 2B:
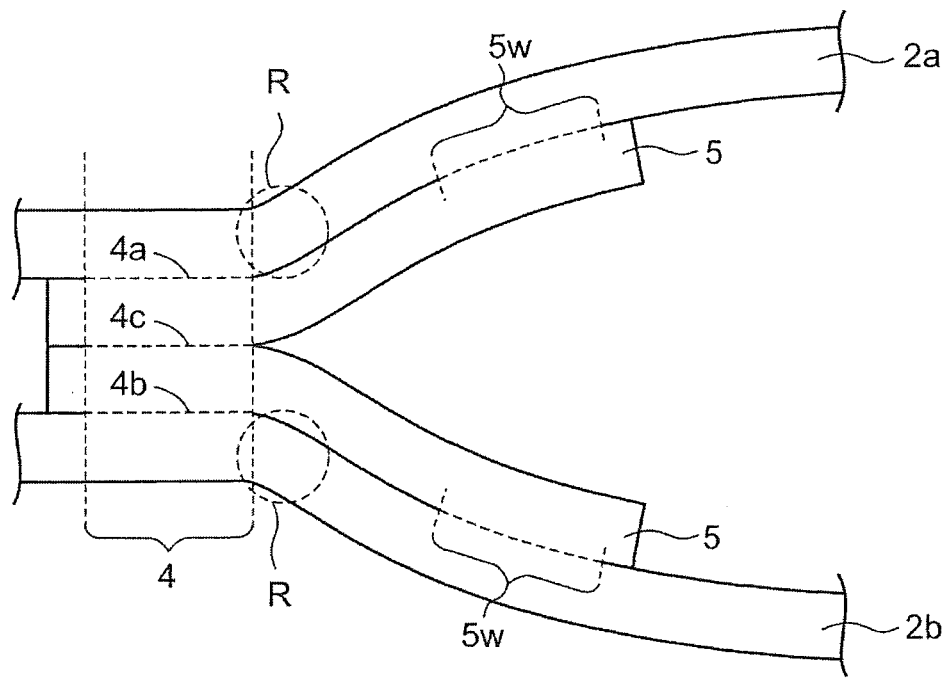
FIG. 2B is a cross-sectional view taken along line A-A' in FIG. 1 (when the airbag is inflated)

FIG. 2A and FIG. 2B are partial cross-sectional views of the airbag 1 taken along line A-A' in FIG. 1. FIG. 2A is a partial cross-sectional view of the airbag 1 in a non-inflated state where air is not supplied to the air chamber of the airbag 1. FIG. 2B is a partial cross-sectional view of the airbag 1 in a state where pressurized air is supplied to the air chamber of the airbag 1 so that the airbag 1 is inflated.

Referring to FIG. 2A, the main sheet member 2a is welded to one of the pair of sub sheet members 5 at the welded portions 4a of the constricted portions 4. The sub sheet members 5 which form a pair are welded to each other at the welded portion 4c of the constricted portion 4. The main sheet member 2b is welded to the other of the pair of sub sheet members 5 at a welded portion 4b of the constricted portion 4. That is, the main sheet members 2a, 2b are collectively welded to each other at the constricted portion 4 with the pair of sub sheet members 5 interposed therebetween.

At the center near portion 5w, the main sheet member 2a is welded to the sub sheet member 5 positioned on an upper side in FIG. 2A, whereas the main sheet member 2b is welded to the sub sheet member 5 positioned on a lower side in FIG. 2A. The sub sheet members 5 which form a pair are not welded to each other in the vicinity of the center near portions 5w.

Accordingly, as shown in FIG. 2B, when a pressurized gas is supplied to the airbag 1, the sub sheet member 5 positioned on an upper side in FIG. 2B is bent upward following the main sheet member 2a, and the sub sheet member 5 positioned on a lower side in FIG. 2B is bent downward following the main sheet member 2b.

When the airbag 1 is in an inflated state (a state where a pressurized gas is supplied to the airbag 1), the airbag 1 is inflated such that the airbag 1 is largely bent in regions R just in the vicinity of the constricted portion 4. Accordingly, when the airbag 1 is in an inflated state, a stress concentration occurs in the regions R of the main sheet members 2a, 2b just in the vicinity of the constricted portion 4. In view of the above, a possibility that the main sheet members 2a, 2b rupture at the regions R is relatively high (compared to portions other than the regions R).

However, according to the airbag 1 of this embodiment, due to an action of the sub sheet members 5 described hereinafter, a stress concentration in the regions R just in the vicinity of the constricted portion 4 is alleviated and hence, strength and durability of the airbag 1 can be enhanced.

The sub sheet member 5 is welded to the main sheet member 2a (or the main sheet member 2b) at the center near portion 5w and the constricted portions 4 and hence, at the time of inflation of the airbag 1, the sub sheet member 5 is deformed following the main sheet member 2a (or the main sheet member 2b). Accordingly, at the time of inflation of the airbag 1, the sub sheet member 5 interacts with the main sheet member 2a at the welded portion (for example, center near portion 5w) such that at least some of a stress acting on the region R in a case where the sub sheet member 5 is not disposed on the main sheet member can be cancelled. That is, at least some of the stress concentrated on the region R of the main sheet member 2a (or the main sheet member 2b) just in the vicinity of the constricted portion are dispersed to other portions (for example, the welded portion 5w) by the sub sheet member 5 and hence, a stress concentration in the region R is alleviated.

In other words, the sub sheet member 5 absorbs at least some of the stress concentrated on the region R of the main sheet member 2a or 2b just in the vicinity of the constricted portion by way of the welded portion (for example, the center near portion 5w), thus alleviating the stress acting on the region R of the main sheet member 2a or the main sheet member 2b. Accordingly, in the airbag 1 of this embodiment, the degree of the stress concentration in the region R just in the vicinity of the constricted portion 4 is alleviated so that strength and durability of the airbag 1 can be enhanced.

Further, as can be understood with reference to FIG. 2A and FIG. 2B, the sub sheet member 5 actually increases a wall thickness of the bag body in the region R just in the vicinity of the constricted portion 4 and hence, the degree of bending in the region R just in the vicinity of the constricted portion 4 at the time of inflation of the bag body can be reduced. Thus, an effect of reducing the degree of fatigue accumulated in the regions R over the years is obtained. Accordingly, it is possible to obtain an effect that strength and durability of the airbag 1 can be enhanced compared to strength and durability of a conventional airbag.

Accordingly, assuming that the main sheet members 2a, 2b of this embodiment are formed using the same material and at the same size as conventional air bags, this embodiment can realize the airbag 1 in which strength and durability is enhanced compared to the conventional airbag.

According to this embodiment, an airbag having substantially the same strength and durability as conventional airbags can be realized by using the main sheet members 2a, 2b formed of material having a lower strength than material for forming the conventional airbags. Accordingly, a manufacturing cost can be further reduced.

According to this embodiment, an airbag having substantially the same strength and durability as conventional airbags can also be realized by using the main sheet members 2a, 2b having a smaller thickness than material for forming the conventional airbags. Accordingly, a manufacturing cost can be further reduced and a weight of the airbag can be further reduced.

Method of Manufacturing Airbag

Next, a method of manufacturing an airbag 1 is described with reference to FIG. 3A to FIG. 3G. The method of manufacturing the airbag 1 described below is merely one example, and the method of manufacturing the airbag 1 is not limited thereto.

In the following example of the method of manufacturing the airbag 1, two layers of the airbag 1 are respectively formed of one sheet. One layer of the airbag 1 is formed of the main sheet member 2a having the opening portions 6, and the other layer of the airbag 1 is formed of the main sheet member 2b. The main sheet member 2a and the main sheet member 2b are welded to each other at peripheral portions thereof, thus forming the bag body.

The method of manufacturing the airbag 1 of this embodiment includes a first welding step and a second welding step. The second welding step is performed after the first welding step. In the first welding step, the main sheet members 2a, 2b and the corresponding sub sheet members 5 are welded to each other at portions of the main sheet members 2a, 2b corresponding to the center near portions 5w.

In the second welding step, the respective main sheet members 2a, 2b and the corresponding sub sheet members 5 are welded to each other at the portions corresponding to the constricted portions 4, thus forming the constricted portions 4 on the main sheet members 2a, 2b. At the same time, the main sheet members 2a, 2b are welded to each other at peripheral edge portions thereof, thus forming the bag body.

In this example of the method of manufacturing the airbag 1, after positioning the main sheet members 2a, 2b and the sub sheet members 5 by welding the main sheet members 2a, 2b and the sub sheet members 5 at the center near portions 5w in the first welding step, the formation of the constricted portions 4 and the formation of the bag body can be performed substantially at the same time. Accordingly, the airbag 1 can be efficiently manufactured.

Figure 3A:
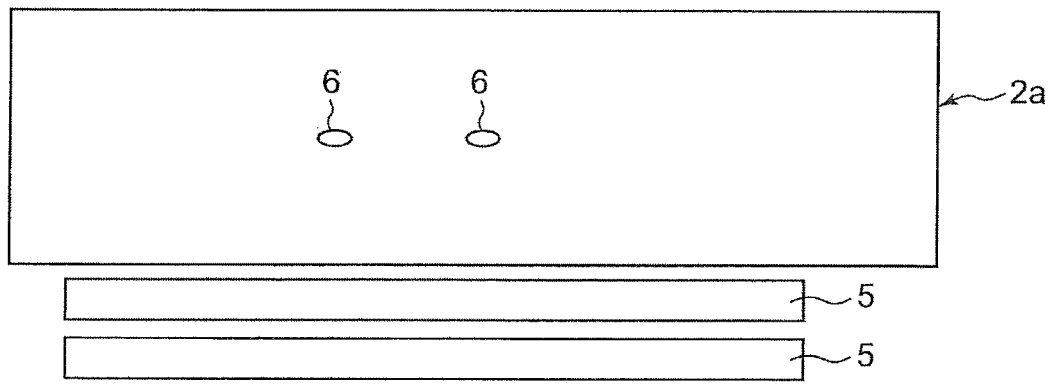
FIG. 3A is a schematic view showing one step of manufacturing the airbag for a blood pressure measuring device.

Firstly, as shown in FIG. 3A, the main sheet member 2a having the opening portions 6 and the sub sheet members 5 are prepared. In this case, at least one of the main sheet member 2a and the sub sheet members 5 may be formed using material containing polyurethane, for example. Further, at least one of the main sheet member 2a and the sub sheet members 5 may be formed using material containing polyvinyl chloride, for example.

Figure 3B:
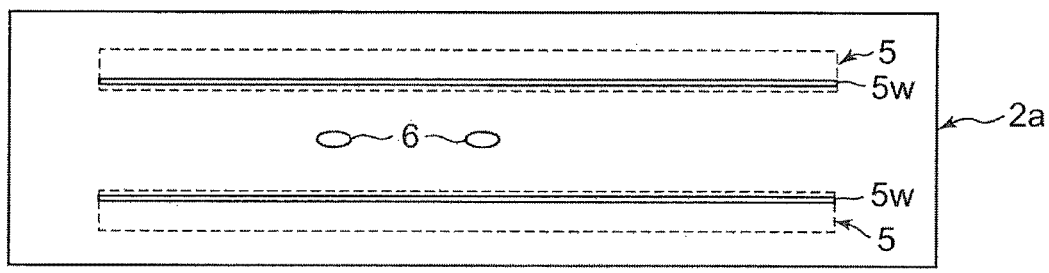
FIG. 3B is a schematic view showing one step of manufacturing the airbag for a blood pressure measuring device.

Then, as shown in FIG. 3B, the main sheet member 2a and the sub sheet members 5 are welded to each other at the center near portions 5w (first welding step).

Figure 3C:
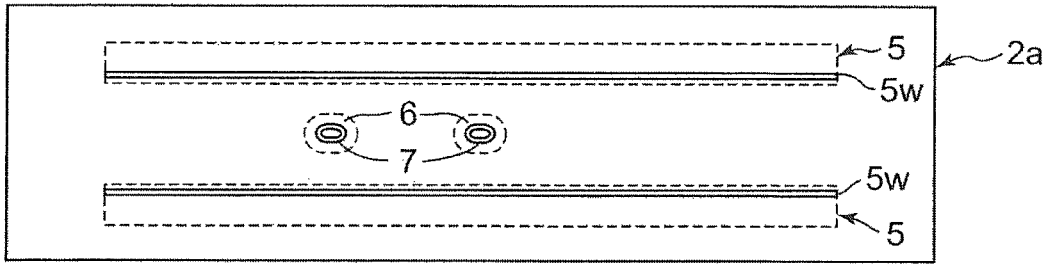
FIG. 3C is a schematic view showing one step of manufacturing the airbag for a blood pressure measuring device.

Subsequently, as shown in FIG. 3C, nipples 7 are welded to the opening portions 6 of the main sheet member 2a.

Figure 3D:
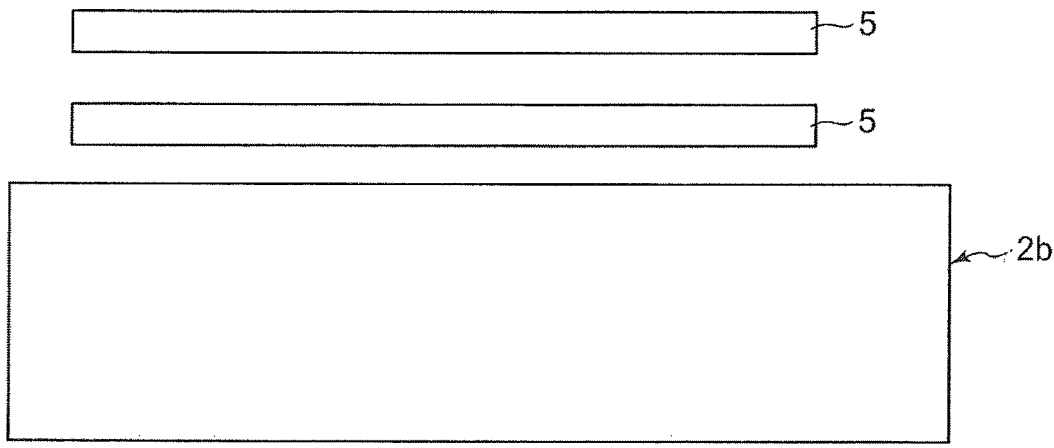
FIG. 3D is a schematic view showing one step of manufacturing the airbag for a blood pressure measuring device.

Next, as shown in FIG. 3D, the main sheet member 2b which is the other layer of the airbag 1 and the sub sheet members 5 are prepared. In this case, at least one of the main sheet member 2b and the sub sheet members 5 may be formed using material containing polyurethane, for example. At least one of the main sheet member 2b and the sub sheet members 5 may be formed using material containing polyvinyl chloride, for example.

Figure 3E:
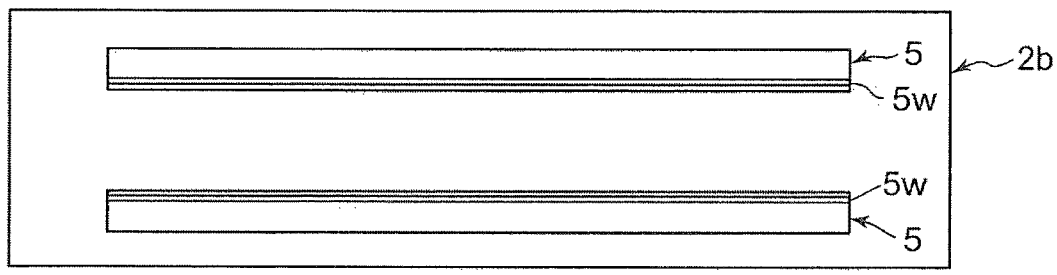
FIG. 3E is a schematic view showing one step of manufacturing the airbag for a blood pressure measuring device.
Figure 3F:
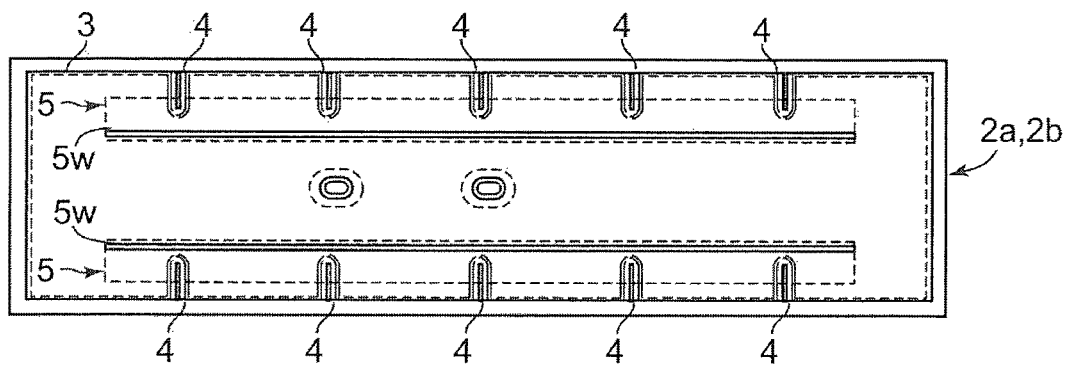
FIG. 3F is a schematic view showing one step of manufacturing the airbag for a blood pressure measuring device.

Then, as shown in FIG. 3E, the main sheet member 2b and the sub sheet members 5 are welded to each other at the center near portions 5w (first welding step).

Lastly, the main sheet member 2a, the pair of sub sheet members 5 which are disposed at positions overlapping with each other as viewed in a plan view, and the main sheet member 2b which is the other layer of the airbag 1 are welded together at the regions corresponding to the constricted portions 4. At the same time, the main sheet member 2a and the main sheet member 2b which is the other layer of the airbag 1 are welded to each other at the peripheral edge portions 3 thereof (second welding step).

Figure 3G:
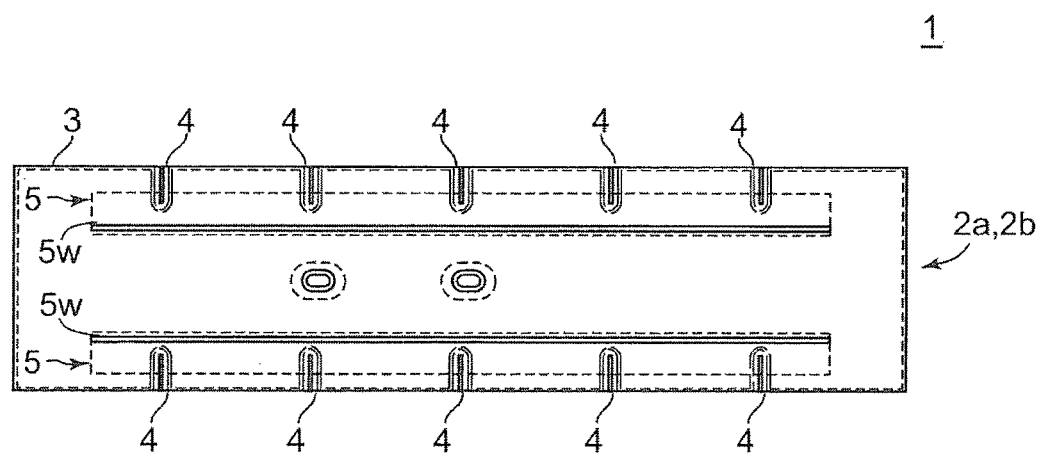
FIG. 3G is a schematic view showing one step of manufacturing the airbag for a blood pressure measuring device.

The welding at the constricted portions 4 and the welding at the peripheral edge portions 3 may be performed separately. Further, as shown in FIG. 3G, portions outside the peripheral edge portions 3 of the main sheet members 2a, 2b may be cut away.

Welding in the first welding step and welding in the second welding step may be high-frequency welding (high-frequency welder) performed at a frequency of 48.5 (MHz) for approximately 4 seconds, for example.

Another Example of Method of Manufacturing Airbag

Next, another example of a method of manufacturing an airbag 1 is described with reference to FIG. 4A to FIG. 4E.

In another example described below, members which are formed into two layers of the airbag 1 (the main sheet members 2a, 2b in the above-mentioned example) are prepared as a single continuous sheet, and a bag body is formed by welding peripheral edge portions of the sheet.

The method of manufacturing the airbag 1 of this embodiment includes a first welding step, a folding step, and a second welding step. The folding step is performed after the first welding step and before the second welding step. In the first welding step, in a state where one continuous sheet (main sheet member 2c) is spread, the main sheet member 2c and the corresponding sub sheet members 5 are welded to each other at portions of the continuous sheet corresponding to center near portions 5w when one sheet is folded into two layers.

Next, in the folding step, the main sheet member 2c is folded such that the main sheet member 2c constitutes two layers of the airbag 1.

Then, in the second welding step, the main sheet member 2c and the corresponding sub sheet members 5 are welded to each other at portions of the main sheet member 2c corresponding to the constricted portions 4, thus forming the constricted portions 4. At the same time, the main sheet member 2c is welded at peripheral edge portions thereof (peripheral portions of the main sheet member 2c which face each other in a state where the main sheet member 2c is folded), thus forming the bag body.

In this example of the method of manufacturing the airbag 1, the pair of sub sheet members 5 can be positioned and disposed with respect to the main sheet members 2c formed of one continuous sheet. Accordingly, a time necessary for manufacturing the airbag can be shortened compared to the case where the respective layers of the main sheet members 2a, 2b and the corresponding sub sheet members 5 are welded to each other at the portions of the two respective layers (two main sheet members 2a, 2c) corresponding to the center near portions 5w.

Figure 4A:
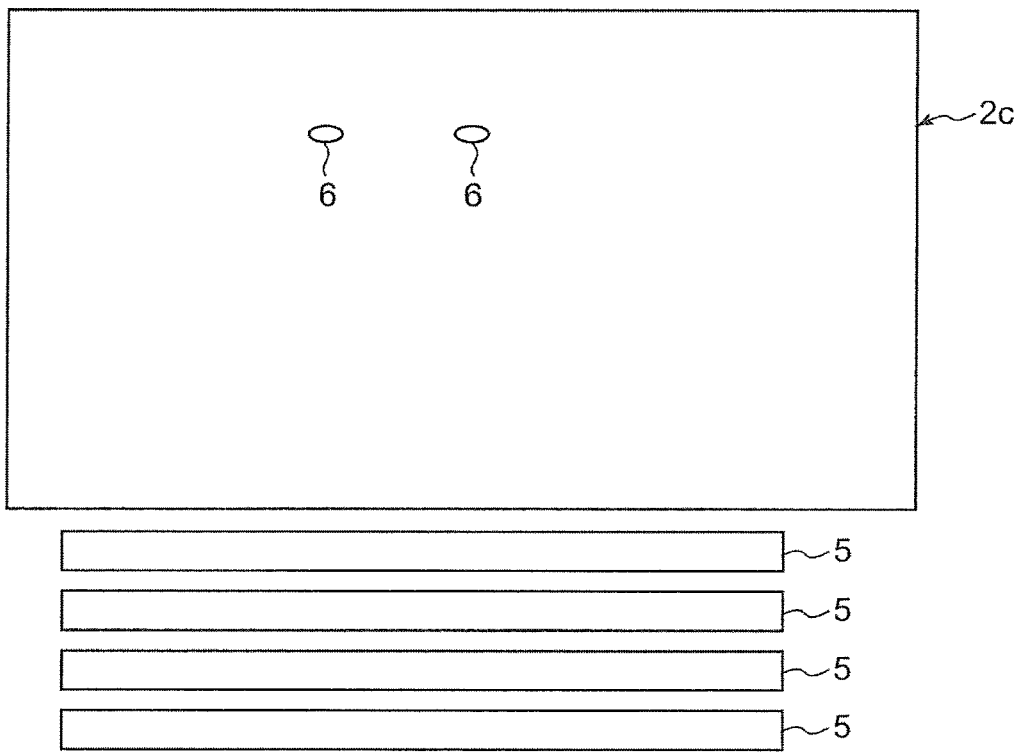
FIG. 4A is a schematic view showing one step of manufacturing an airbag for a blood pressure measuring device of another example.

Firstly, as shown in FIG. 4A, the main sheet member 2c having opening portions 6 and the sub sheet members 5 are prepared. In this case, at least one of the main sheet member 2c and the sub sheet members 5 may be formed using material containing polyurethane, for example. Further, at least one of the main sheet member 2c and the sub sheet members 5 may be formed using material containing polyvinyl chloride, for example.

Figure 4B:
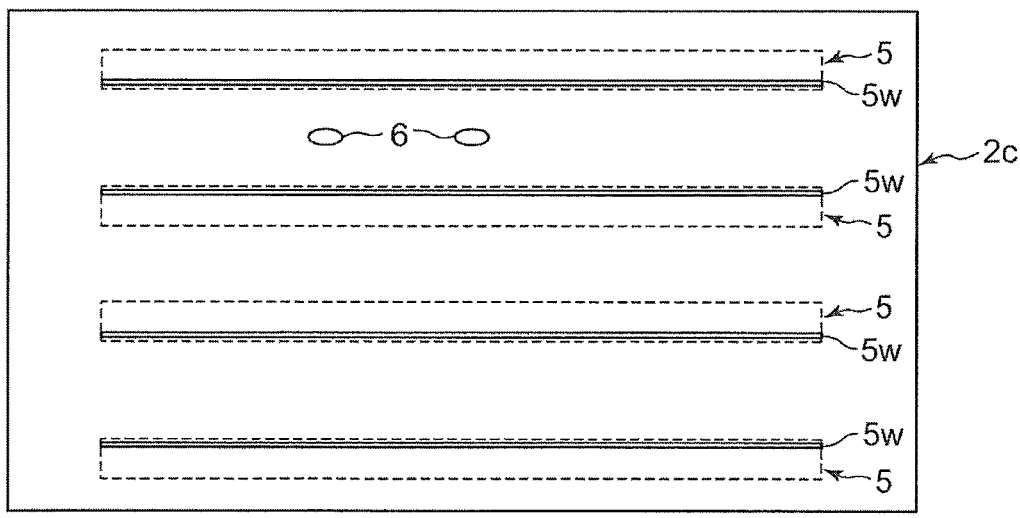
FIG. 4B is a schematic view showing one step of manufacturing an airbag for a blood pressure measuring device of another example.

Then, as shown in FIG. 4B, the main sheet member 2c and the sub sheet members 5 are welded to each other at the center near portions 5w (first welding step).

Figure 4C:
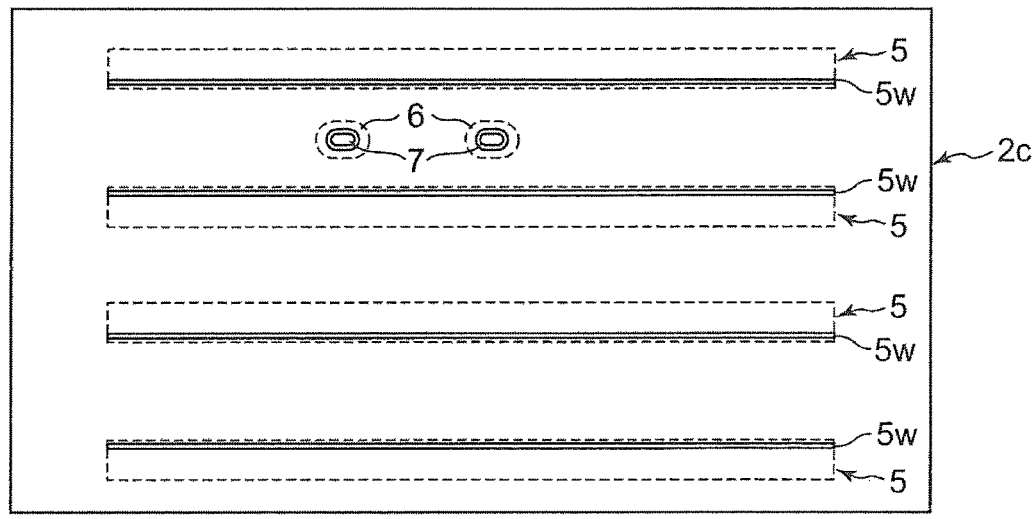
FIG. 4C is a schematic view showing one step of manufacturing an airbag for a blood pressure measuring device of another example.

Subsequently, as shown in FIG. 4C, nipples 7 are welded to the opening portions 6 of the main sheet member 2c.

Figure 4D:
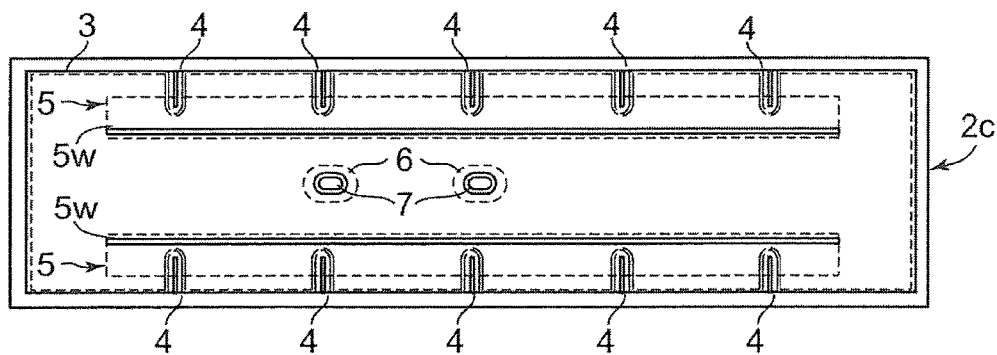
FIG. 4D is a schematic view showing one step of manufacturing an airbag for a blood pressure measuring device of another example.

Next, as shown in FIG. 4D, the main sheet member 2c is folded back so as to form two layers which overlap with each other (folding back step).

Lastly, two layers of the folded main sheet member 2c and the pair of sub sheet members 5 which are disposed at positions where the sub sheet members 5 overlap with each other as viewed in a plan view are welded to each other in regions corresponding to the constricted portions 4. At the same time, two layers of the main sheet member 2c which face each other are welded to each other at peripheral edge portions 3 thereof in a folded state (second welding step).

Figure 4E:
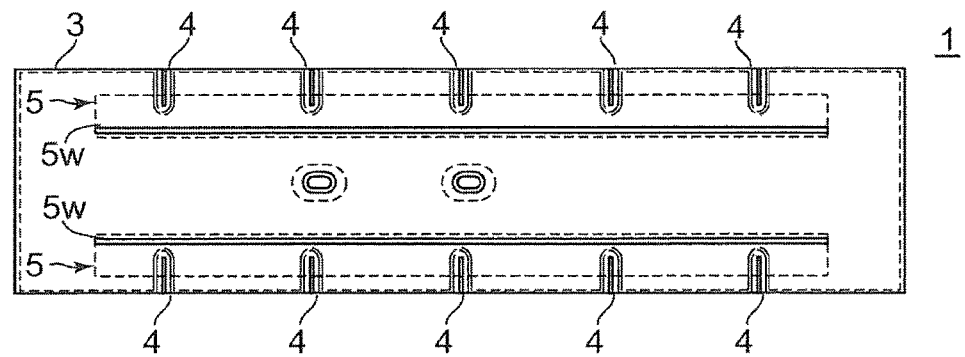
FIG. 4E is a schematic view showing one step of manufacturing an airbag for a blood pressure measuring device of another example.
Figure 5A:
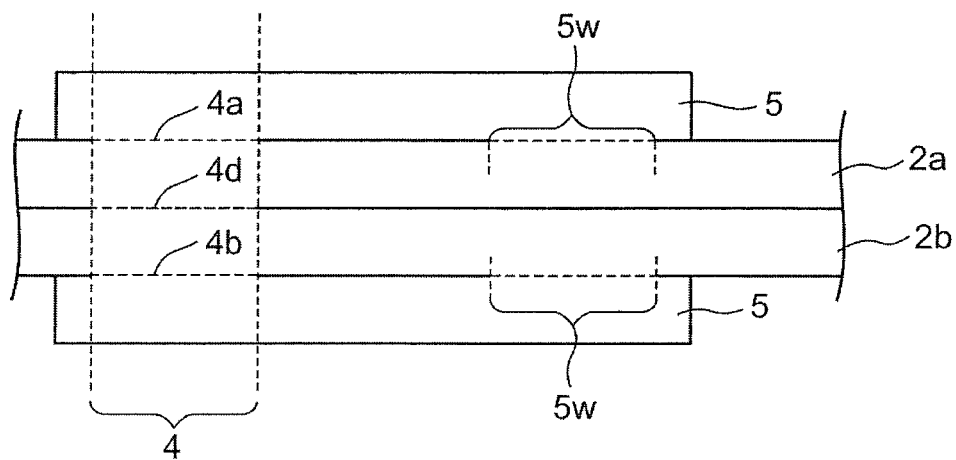
FIG. 5A is a cross-sectional view of an area in the vicinity of a constricted portion of an airbag for a blood pressure measuring device according to a modification (when the airbag is not inflated)
Figure 5B:
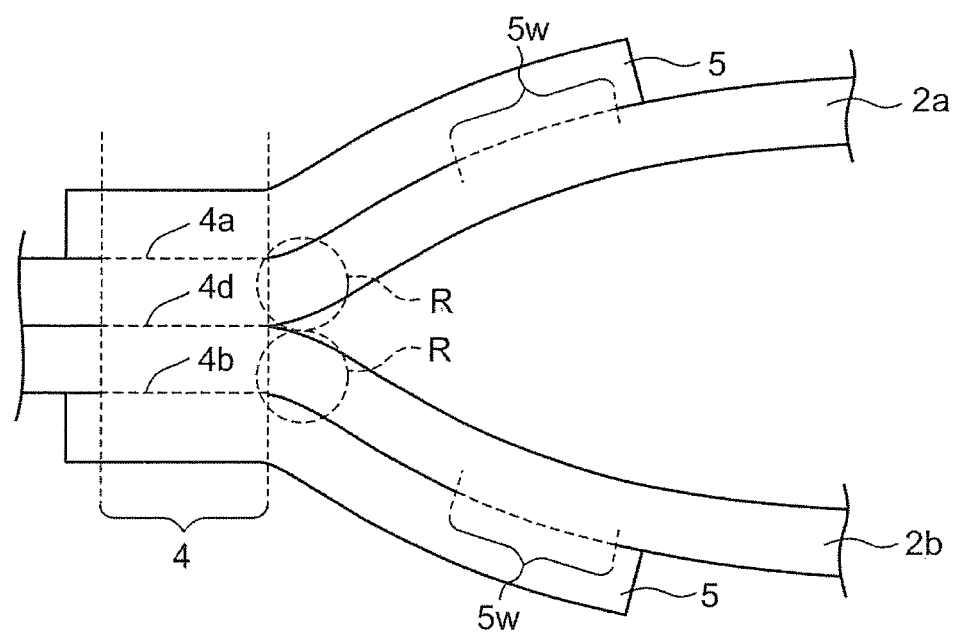
FIG. 5B is a cross-sectional view of the area in the vicinity of the constricted portion of the airbag for a blood pressure measuring device according to the modification (when the airbag is inflated)
Figure 6:
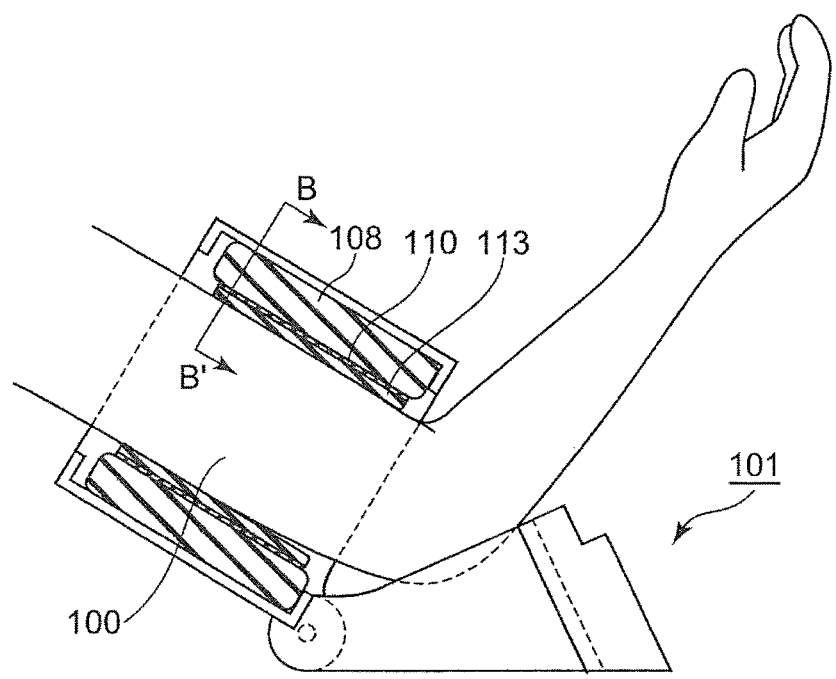
FIG. 6 is a schematic view showing an in-use mode of the blood pressure measuring device.
Figure 7:
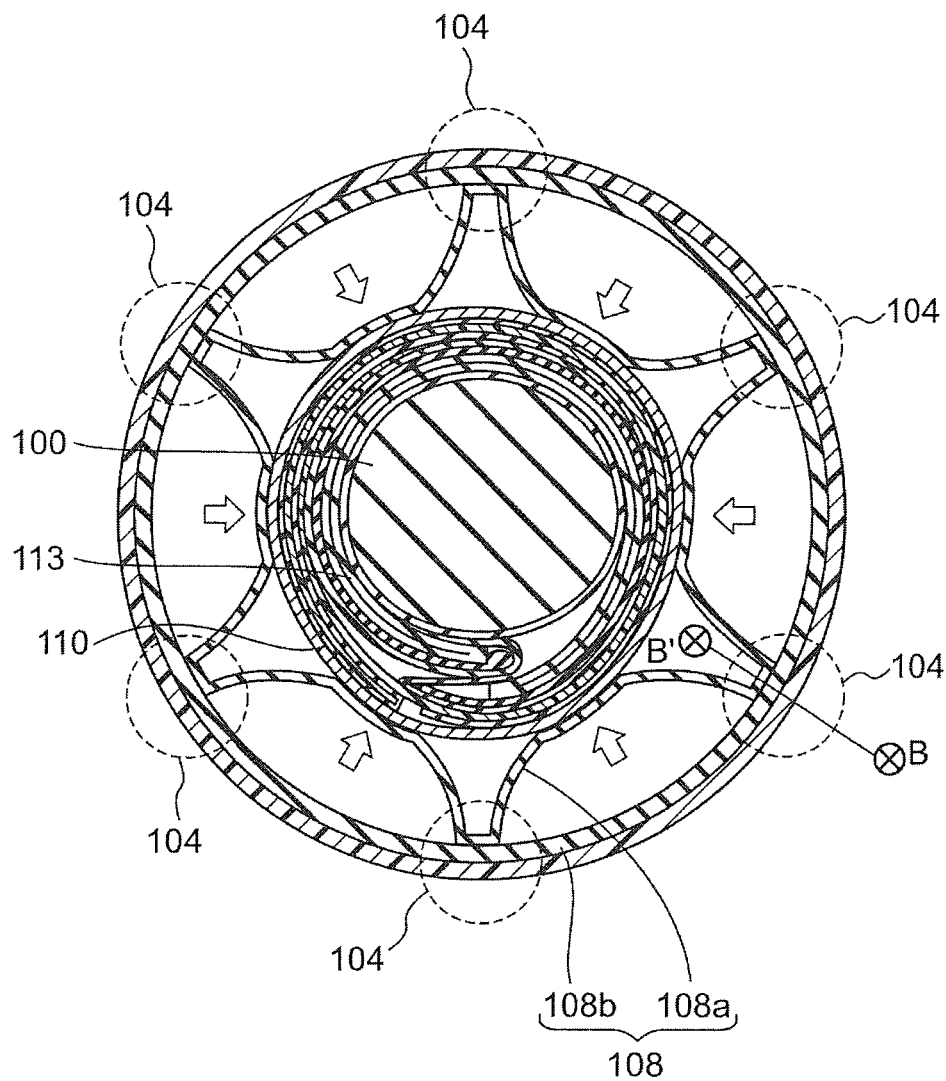
FIG. 7 is a view showing a state where the airbag is inflated, and a cuff is fixed to an upper arm portion inserted into the blood pressure measuring device.
Figure 8A:
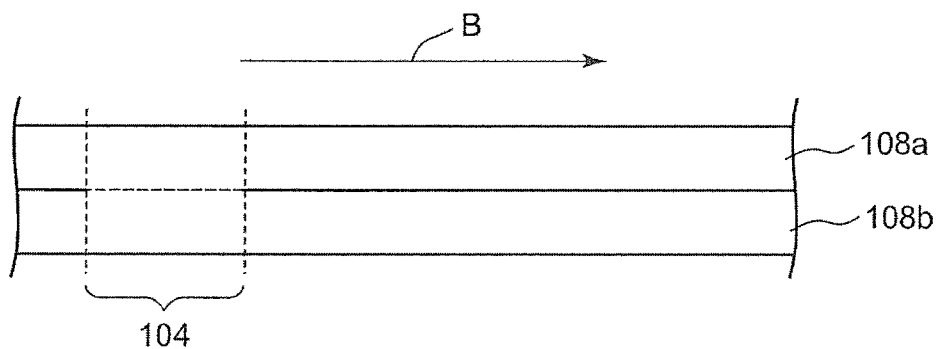
FIG. 8A is a cross-sectional view of an area in the vicinity of a constricted portion of a conventional airbag for a blood pressure measuring device taken along line B-B' in FIG. 6 and FIG. 7 (when the airbag is not inflated)
Figure 8B:
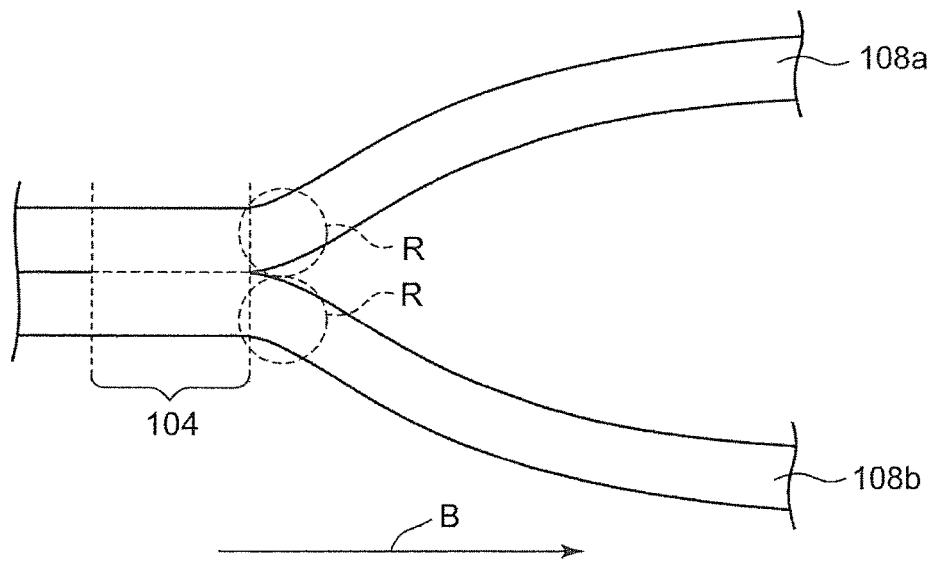
FIG. 8B is a cross-sectional view of the area in the vicinity of the constricted portion of the conventional airbag for a blood pressure measuring device taken along line B-B' in FIG. 6 and FIG. 7 (when the airbag is inflated).

The welding at the constricted portions 4 and the welding at the peripheral edge portions 3 may be performed separately. Further, as shown in FIG. 4E, portions outside the peripheral edge portions 3 of the main sheet members 2c in a folded state may be cut away.

The welding in the first welding step and the welding in the second welding step may be high-frequency welding (high-frequency welder) performed at a frequency of 48.5 (MHz) for approximately 4 seconds, for example.

Modification of Airbag

Lastly, a modification of the airbag 1 is described. The airbag 1 of this modification differs from the above-mentioned airbag 1 in that the sub sheet member 5 is welded to the main sheet member 2a or 2b which correspond to the sub sheet member 5 at the center near portion 5w outside the bag body. Except for this point, the above-mentioned airbag 1 and the airbag 1 of the modification may be substantially equal to each other. The airbag 1 of this modification can obtain the same effects as the above-mentioned airbag 1. Further, material for forming the members, a spaced-apart distance, a wall thickness of the members and the like may be set equal to those of the above-mentioned airbag 1.

With respect to the airbag according to the embodiment of the present invention, one of the pair of sub sheet members 5 may be disposed by welding to the main sheet member 2a or to the main sheet member 2b outside the airbag 1, and the other of the pair of sub sheet members 5 may be disposed by welding to the main sheet member 2a or to the main sheet member 2b inside the airbag 1. Also in this case, it is expected that the airbag can obtain the same effects as the above-mentioned airbag 1.

The airbag according to a first aspect of the present invention is an airbag for a blood pressure measuring device for fixing a blood pressure measuring cuff to an upper arm portion of a person to be measured, the airbag including:

a main sheet member which spreads in two layers in a longitudinal direction and in a width direction perpendicular to the longitudinal direction so as to form a bag body which defines an air chamber therein, wherein at least one constricted portion is formed locally on the bag body with respect to the longitudinal direction of the bag body, the constricted portion being formed by welding the two layers of the main sheet member so as to narrow a size of the air chamber with respect to the width direction, a pair of sub sheet members are disposed so as to correspond to an inside or an outside of the respective layers of the main sheet member, the sub sheet member occupying a wider region than the constricted portion including at least a portion corresponding to the constricted portion, and the pair of sub sheet members are respectively welded to the corresponding layers of the main sheet member at a portion corresponding to the constricted portion, the pair of sub sheet members being welded to the corresponding layers of the main sheet member at a center near portion away from the constricted portion toward a center side with respect to the width direction.

In the airbag for a blood pressure measuring device according to the first aspect of the present invention, the bag body is formed of the main sheet member which spreads in two layers in the longitudinal direction and in the width direction, and at least one constricted portion is formed locally on the bag body with respect to the longitudinal direction of the bag body, the constricted portion being formed by welding the two layers of the main sheet member so as to narrow a size of the air chamber with respect to the width direction. In the constricted portion, a pair of sub sheet members are disposed so as to correspond to an inside or an outside of the respective layers of the main sheet member, the sub sheet member occupying a wider region than the constricted portion including at least a portion corresponding to the constricted portion. The pair of sub sheet members are respectively welded to the corresponding layers of the main sheet member at a portion corresponding to the constricted portion, and the pair of sub sheet members are welded to the corresponding layers of the main sheet member at a center near portion which is away from the constricted portion toward a center side with respect to the width direction.

The sub sheet members disposed in this manner and welded to the main sheet member are bonded to the main sheet member at the constricted portion and at the center near portions such that the sub sheet members extend over the region of the main sheet member in the vicinity of the constricted portion. With such a configuration, the sub sheet members absorb, by way of the center near portion, at least some of the stress acting on the region of the main sheet member in the vicinity of the constricted portion at the time of inflation of the bag body. Accordingly, it is possible to obtain an effect that the magnitude of the stress acting at the time of inflation of the bag body on the region of the main sheet member in the vicinity of the constricted portion can be reduced in comparison to the case where the sub sheet members are not disposed on the main sheet member. Further, the sub sheet members can actually increase a wall thickness of the bag body in the region in the vicinity of the constricted portion and hence, the degree of bending in the region in the vicinity of the constricted portion at the time of inflation of the bag body can be reduced. Thus, an effect of reducing the degree of fatigue accumulated in the region over the years is obtained. Accordingly, the airbag for a blood pressure measuring device can obtain an effect that the strength and the durability of an airbag can be enhanced compared to conventional airbags.

In the airbag for a blood pressure measuring device according to an embodiment, the bag body may include a plurality of constricted portions in the longitudinal direction, and the pair of sub sheet members may be respectively disposed to extend over portions corresponding to two or more constricted portions.

In the airbag for a blood pressure measuring device according to the embodiment, one sub sheet member can be disposed so as to include the portions corresponding to the plurality of constricted portions. With such a configuration, compared to the case where the sub sheet members separated from each other are respectively disposed for respective constricted portions, in the manufacturing steps, the number of man-hours for positioning the sub sheet members with respect to the main sheet members can be reduced. Further, the number of sub sheet members necessary for manufacturing one airbag can be reduced. Further, it is possible to press the curler uniformly along the circumferential direction at the time of measuring a blood pressure.

In the airbag for a blood pressure measuring device according to an embodiment, a distance that the sub sheet member is away from the constricted portion may be equal to or larger than a sum of a wall thickness of one main sheet member and a wall thickness of one sub sheet member.

In the airbag for a blood pressure measuring device according to the embodiment, it is possible to further increase a bag-body strength enhancing effect.

In the airbag for a blood pressure measuring device according to an embodiment, the pair of sub sheet members may be respectively disposed on inner sides of the two layers of the main sheet member.

In the airbag for a blood pressure measuring device according to the embodiment, the sub sheet members are disposed on the inner side of the bag body and hence, an outer shape of the airbag can be made smooth at the same level as the case where the sub sheet members are not disposed on the main sheet member.

In the airbag for a blood pressure measuring device according to an embodiment, a size of the sub sheet member in a direction which agrees with the width direction of the main sheet member in a state where the sub sheet member is disposed on the main sheet member is smaller than a size of the main sheet member in the width direction.

In the airbag for a blood pressure measuring device according to the embodiment, the size of the sub sheet member can be narrowed and hence, it is possible to obtain an effect that a manufacturing cost can be reduced compared to the case where the sub sheet member has substantially the same size as the main sheet member.

In the airbag for a blood pressure measuring device according to an embodiment, the two layers of the main sheet member may be respectively formed of one sheet, and the bag body may be formed by welding a peripheral edge portion of one of the sheets and a peripheral edge portion of the other of the sheets.

The method of manufacturing an airbag for a blood pressure measuring device according to a second aspect of the present invention is a method of manufacturing the airbag for a blood pressure measuring device according to the above embodiment, the method including:

a first welding of welding the two layers of the main sheet member and the corresponding sub sheet members at portions of the two layers of the main sheet member corresponding to center near portions; and a second welding of, after the first welding, forming the constricted portions by welding the two respective layers of the main sheet member and the corresponding sub sheet members at portions of the two respective layers of the main sheet member corresponding to the constricted portions and, simultaneously, forming the bag body by welding the two respective layers of the main sheet member at the peripheral edge portions of the sheet.

In the method of manufacturing an airbag for a blood pressure measuring device according to the second aspect, after positioning the main sheet member and the sub sheet members by welding the main sheet member and the sub sheet members at the center near portions in the first welding, the formation of the constricted portions and the formation of the bag body can be performed substantially at the same time. Accordingly, the airbag for a blood pressure measuring device according to the first aspect can be efficiently manufactured.

The method of manufacturing an airbag for a blood pressure measuring device according to a third aspect of the present invention is a method of manufacturing the airbag for a blood pressure measuring device according to the above embodiment, the method including:

a first welding of welding the respective layers of the main sheet member and the corresponding sub sheets to each other at a portion corresponding to a center near portion of one continuous sheet corresponding to the two layers of the main sheet member;

a folding of, after the first welding, folding the one continuous sheet so as to form the two layers of the main sheet member; and a second welding of, after the folding, forming the constricted portions by welding the two respective layers of the main sheet member and the corresponding sub sheet members at portions of the two layers of the main sheet member corresponding to the constricted portions and, simultaneously, forming the bag body by welding the corresponding peripheral edge portions of the folded one sheet.

In the method of manufacturing an airbag for a blood pressure measuring device according to the third aspect of the present invention, a pair of sub sheet members can be positioned and disposed with respect to the main sheet member formed of one continuous sheet. Accordingly, a time necessary for manufacturing the airbag for a blood pressure measuring device can be shortened compared to the case where the respective layers of the main sheet member and the corresponding sub sheet members are welded to each other at the portions of two respective layers of the main sheet member (two main sheet members) corresponding to the center near portions.

As can be clearly understood from the above, according to the airbag for a blood pressure measuring device of the embodiment of the present invention, the sub sheet members absorb at least some of the stress acting on the regions of the main sheet member in the vicinity of the constricted portions at the time of inflation of the bag body and hence, it is possible to obtain an effect that the magnitude of the stress acting on the regions of the main sheet member in the vicinity of the constricted portions can be reduced in comparison to the case where the sub sheet members are not disposed on the main sheet member. Accordingly, the airbag for a blood pressure measuring device can obtain an effect that the strength and the durability of the airbag can be enhanced compared to conventional airbags.

Further, according to the method of manufacturing an airbag for a blood pressure measuring device of the embodiment of the present invention, after positioning the main sheet member and the sub sheet members by welding the main sheet member and the sub sheet members at the center near portions in the first welding step, the formation of the constricted portions and the formation of the bag body can be performed substantially at the same time and hence, the above-mentioned airbag for a blood pressure measuring device can be efficiently manufactured.

What is claimed is:

1. An airbag for a blood pressure measuring device for fixing a blood pressure measuring cuff to an upper arm portion of a person to be measured, the airbag comprising:
    a first main sheet member having first peripheral edge portions;
    a second main sheet member having second peripheral edge portions,
    wherein the first and second main sheet members are welded or bonded together at the first and second peripheral edge portions to form a bag body, which defines an air chamber therein, the bag body having a longitudinal direction and a width direction perpendicular to the longitudinal direction, and the first and second peripheral edge portions each including a longitudinal side that extends in the longitudinal direction;
    at least one constricted portion formed by welding a specified area of the first main sheet member, which includes a specified portion of the longitudinal side and extends in the width direction toward a center of the bag body, to a specified area of the second main sheet member, which corresponds to the specified area of the first main sheet member, to narrow a size of the air chamber in the width direction at a location of the at least one constricted portion, the location of the at least one constricted portion being narrower than the overall width of the air chamber;
    a first sub sheet member and a second sub sheet member respectively corresponding to the first main sheet member and the second main sheet member, each of the first and the second sub sheet members being disposed inside or outside of a corresponding main sheet member of the first and second main sheet members, occupying a wider region than the at least one constricted portion including the at least one constricted portion,
    wherein the first and second sub sheet members are stacked and welded or bonded to the first and second main sheet members at the at least one constricted portion, and at a distance away from the longitudinal side of the corresponding main sheet member, each of the first and second sub sheet members being welded or bonded to the corresponding main sheet member at a center near portion, the center near portion being distanced away from the at least one constricted portion in the width direction toward the center of the bag body.

2. The airbag for a blood pressure measuring device according to claim 1, wherein the bag body includes a plurality of the constricted portions in the longitudinal direction, and the first and second sub sheet members are respectively disposed to traverse portions corresponding to two or more of the constricted portions.

3. The airbag for a blood pressure measuring device according to claim 1, wherein a distance between the constricted portion and the center near portion in the width direction is equal to or larger than a sum of a wall thickness of one main sheet member and a wall thickness of one sub sheet member.

4. The airbag for a blood pressure measuring device according to claim 1, wherein the first and second sub sheet members are respectively disposed on inner sides of the first and second main sheet member.

5. The airbag for a blood pressure measuring device according to claim 1, wherein a size of each of the first and second sub sheet members in the width direction of the bag body in a state where each of the first and second sub sheet member is disposed on the corresponding main sheet member is smaller than a size of the corresponding main sheet member in the width direction.

6. The airbag for a blood pressure measuring device according to claim 1,
   wherein the first and second main sheet member are respectively formed of one sheet, and
   wherein the bag body is formed by welding together the first peripheral edge portion of the first main sheet member and the second peripheral edge portion of the second main sheet member.

7. A method of manufacturing the airbag for a blood pressure measuring device according to claim 6, the method comprising:
   a first welding step of welding each of the first and second sub sheet members to the corresponding first and second main sheet members at the center near portion; and
   a second welding step of, after the first welding step, forming the at least one constricted portion by stacking and welding the first and second main sheet members and the first and second sub sheet members at the specified area corresponding to the at least one constricted portion and, simultaneously, forming the bag body by welding together the first and second main sheet members at the first and second peripheral edge portions.

8. A method of manufacturing the airbag for a blood pressure measuring device according to claim 1, the method comprising:
   a first welding step of preparing one continuous sheet to be folded into two layers as the first and second main sheet members, and welding each of the first and second sub sheet members to the corresponding main sheet member at a portion corresponding to the center near portion when the one continuous sheet is folded into two layers as the first and second main sheet members;
   a folding step of, after the first welding step, folding the one continuous sheet into two layers to form the first and second main sheet members; and
   a second welding step of, after the folding step, forming the at least one constricted portion by stacking and welding the first and second main sheet members and the first and second sub sheet members at the specified area corresponding to the at least one constricted portion and, simultaneously, forming the bag body by welding together the first and second main sheet members at the first and second peripheral edge portions.

* * * * *